(12) United States Patent
Ito et al.

(10) Patent No.: US 7,687,279 B2
(45) Date of Patent: Mar. 30, 2010

(54) EVALUATION METHOD FOR CHEMICAL SOLUTION, QUALIFICATION METHOD FOR CHEMICAL SOLUTION AND METHOD FOR MANUFACTURING SEMICONDUCTOR DEVICE

(75) Inventors: Shinichi Ito, Yokohama (JP); Eishi Shiobara, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 1385 days.

(21) Appl. No.: 11/105,362

(22) Filed: Apr. 14, 2005

(65) Prior Publication Data

US 2005/0244979 A1    Nov. 3, 2005

(30) Foreign Application Priority Data

Apr. 14, 2004 (JP) .............................. 2004-119363

(51) Int. Cl.
*G01N 33/00* (2006.01)
(52) U.S. Cl. .................................................... 436/183
(58) Field of Classification Search ................. 436/183
See application file for complete search history.

(56) References Cited

U.S. PATENT DOCUMENTS

| | | | |
|---|---|---|---|
| 6,184,983 | B1 | 2/2001 | Yamaguchi et al. |
| 6,268,013 | B1 | 7/2001 | Akimoto et al. |
| 6,748,815 | B2 | 6/2004 | Povey et al. |

FOREIGN PATENT DOCUMENTS

| | | | |
|---|---|---|---|
| JP | 9-273987 | | 10/1997 |
| JP | 2003-315245 | * | 6/2003 |
| JP | 3476080 B2 | | 9/2003 |
| JP | 3476081 B2 | | 9/2003 |
| JP | 3476082 B2 | | 9/2003 |
| JP | 3485182 B1 | | 10/2003 |
| JP | 3485183 B1 | | 10/2003 |
| JP | 2003-315245 | | 11/2003 |

OTHER PUBLICATIONS

Notification of Reasons for Rejection from the Japanese Patent Office, dated Oct. 31, 2006, in counterpart Japanese Patent Application No. 2004-119363.

* cited by examiner

*Primary Examiner*—Sam P Siefke
(74) *Attorney, Agent, or Firm*—Finnegan, Henderson, Farabow, Garrett & Dunner, LLP

(57) ABSTRACT

A method for evaluating chemical solution includes determining number of particles in liquid for each size of the particles by measurement, expressing a relationship between size of the particles and number of particles corresponding to the size by a function based on the number of particles for each size of the particles determined by the measurement, and evaluating influence of particles having size less than or equal to a measurement limit in the liquid based on the function.

4 Claims, 5 Drawing Sheets

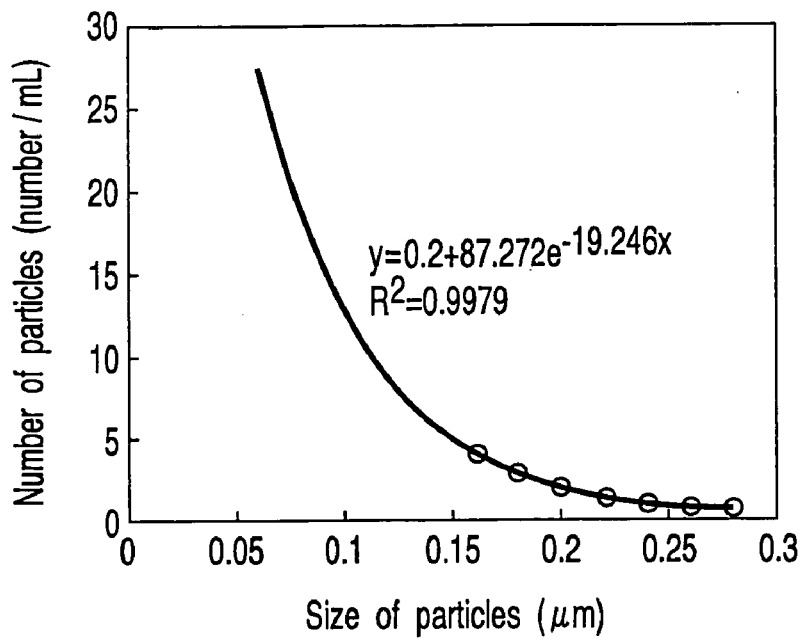
F I G. 1
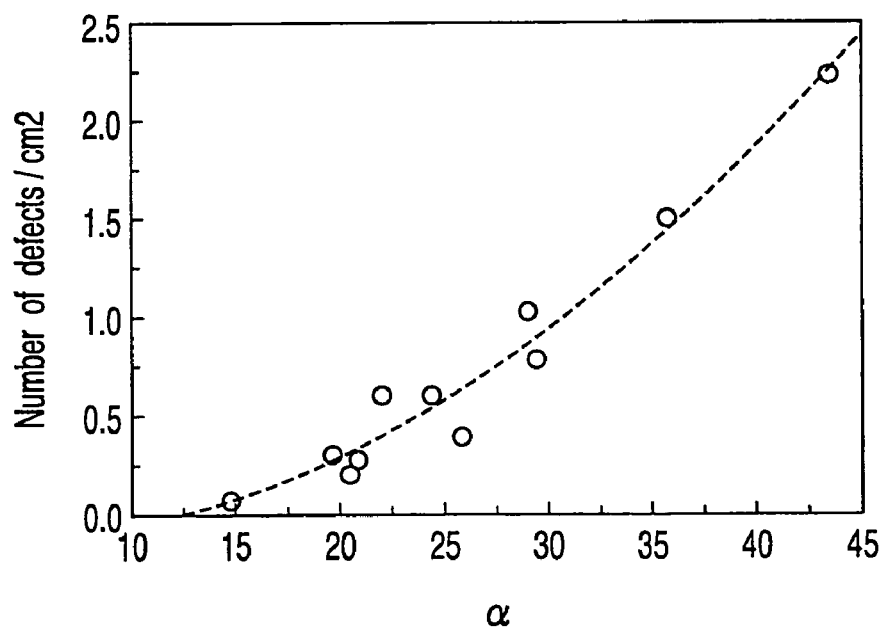
F I G. 2

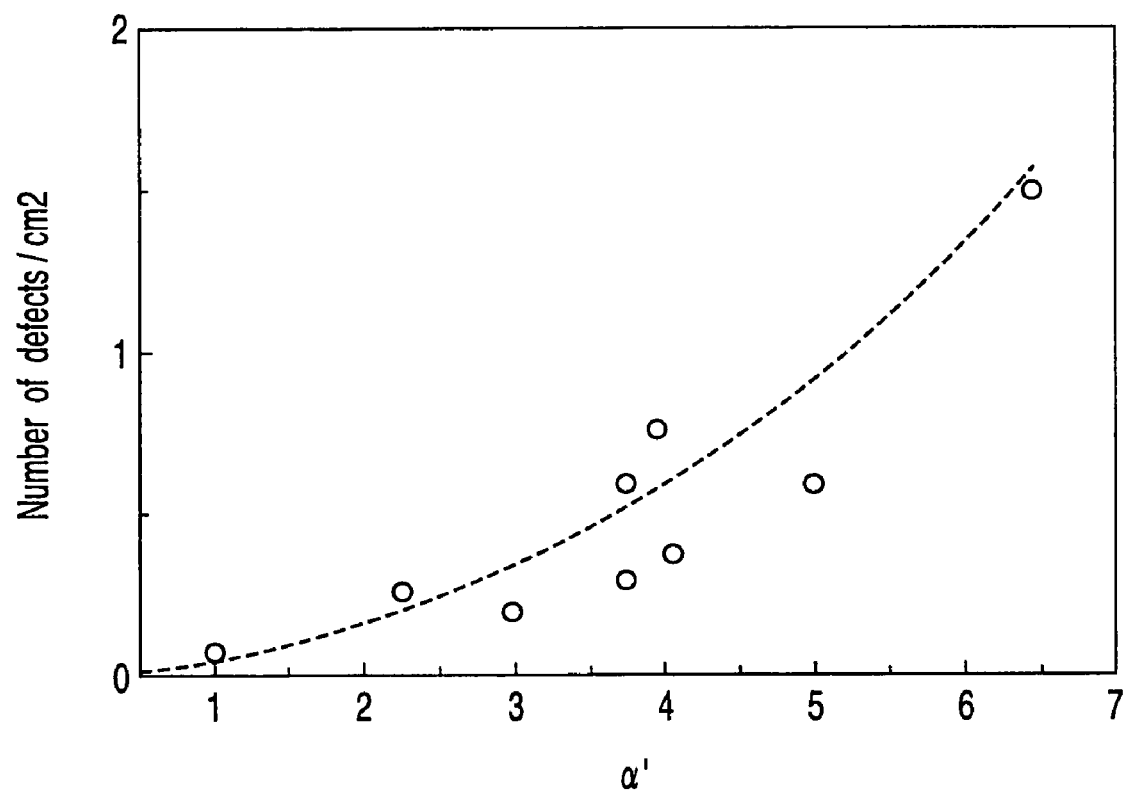
F I G. 3

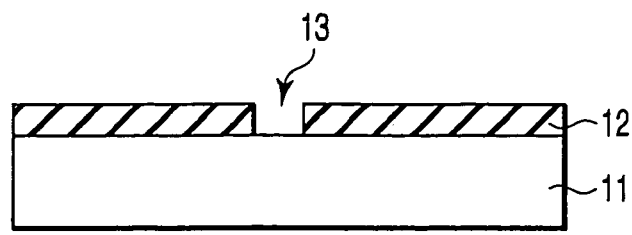
F I G. 4 A
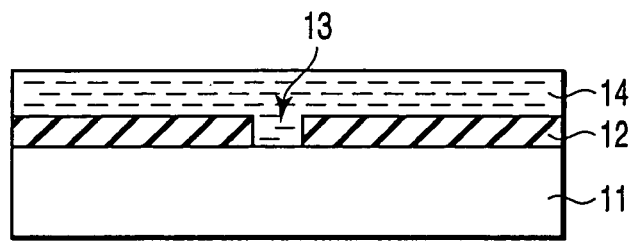
F I G. 4 B
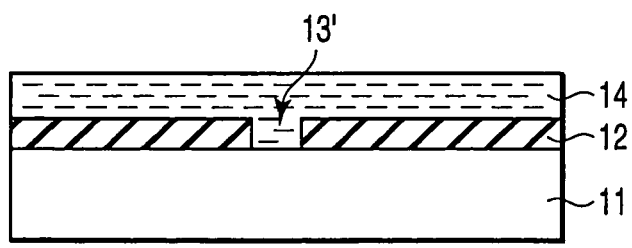
F I G. 4 C
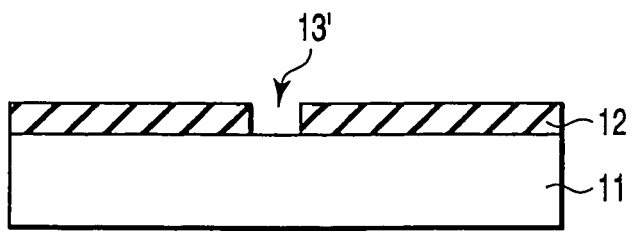
F I G. 4 D

EVALUATION METHOD FOR CHEMICAL SOLUTION, QUALIFICATION METHOD FOR CHEMICAL SOLUTION AND METHOD FOR MANUFACTURING SEMICONDUCTOR DEVICE

CROSS-REFERENCE TO RELATED APPLICATIONS

This application is based upon and claims the benefit of priority from prior Japanese Patent Application No. 2004-119363, filed Apr. 14, 2004, the entire contents of which are incorporated herein by reference.

BACKGROUND OF THE INVENTION

1. Field of the Invention

The present invention relates to an evaluation and qualification method for chemical solution used for a semiconductor manufacturing process, and a method for manufacturing a semiconductor device.

2. Description of the Related Art

Quality assurance of liquid is carried out by controlling the size and number of particles in the liquid. The size and number are measured by a particle counter for counting particles in liquid (Jpn. Pat. Appln. KOKAI Publication No. 9-273987). The particle counter measures the number of particles having size within a predetermined range. As it is extremely difficult to measure fine particles in liquid, the number of particles of all size existing in the liquid is not necessarily measured.

Table 1 is one example of a table showing quality assurance of liquids. This is prepared by a resist maker, and shows the quality assurance of resist solutions.

TABLE 1

|  |  | Per-missible number | Measured number | | |
|---|---|---|---|---|---|
|  |  |  | Lot number 1 | Lot number 2 | Lot number 3 |
| Size | 0.2-0.3 μm | 10 | 4 | 9 | 20 |
|  | 0.3 μm | 2 | 1 | 1 | 3 |
| Solution acceptance/rejection determination | | | Acceptable | Acceptable | Rejectable |

In Table 1, the measured values of the number of particles with respect to three types of resist lots are shown. Usually, in the quality assurance of liquids, as shown in Table 1, the number of particles which is permitted (permissible number) is provided with respect to the ranges of a plurality of particle sizes (two ranges of a range which is greater than or equal to 0.2 μm and less than 0.3 μm, and a range which is greater than or equal to 0.3 μm in Table 1). In Table 1, the example is shown in which particles greater than or equal to 0.2 μm and less than 0.3 μm are permitted up to ten, and particles greater than or equal to 0.3 μm are permitted up to two.

The resist maker selects lot numbers which can be shipped on the basis of Table 1. In Table 1, with respect to a lot number 1 and a lot number 2, the number of the particles which have been measured are within the permissible number of particles with respect to the both of the two ranges of particle sizes. However, the number of the particles in a lot number 3 exceeds the permissible number of particles. Accordingly, solution acceptance/rejection determinations result in acceptance for lot number 1 and lot number 2, and in rejection for lot number 3, and the resist solutions of lot number 1 and lot number 2 are shipped.

Users will purchase resist solutions which have been determined to be acceptable as described above from the resist maker. However, the use of a solution determined to be acceptable does not necessarily result in a great reduction of defects on a resist pattern, for example, a short circuit system defect, an opening system defect, or the like. The same thing can be said with respect to other chemical solution such as a solution including low dielectric constant material, a solution including ferroelectric material, and the like as well.

BRIEF SUMMARY OF THE INVENTION

According to an aspect of the present invention, there is provided a method for evaluating chemical solution comprising: determining number of particles in liquid for each size of the particles by measurement; expressing a relationship between size of the particles and number of particles corresponding to the size by a function based on the number of particles for each size of the particles determined by the measurement; and evaluating influence of particles having size less than or equal to a measurement limit in the liquid based on the function.

According to an aspect of the present invention, there is provided a method for qualifying chemical solution comprising: determining number of particles in liquid for each size of the particles by measurement; expressing a relationship between size of the particles and number of particles corresponding to the size by a function based on the number of particles for each size of the particles determined by the measurement; evaluating influence of particles having size less than or equal to a measurement limit in the liquid based on the function, and determining whether the liquid is acceptable or rejectable; and qualifying the liquid as a chemical solution in a case where the liquid is determined acceptable in the determining whether the liquid is acceptable or rejectable.

According to another aspect of the present invention, there is provided a method for qualifying chemical solution comprising: determining number of particles in liquid for each size of the particles by a particle counter for counting particles in liquid; expressing a relationship between size of the particles and number of the particles corresponding to the size as an exponential function or a power function; comparing at least one coefficient of a coefficient of the exponential function and an exponent of the power function, and a predetermined value; and qualifying the liquid as a chemical solution used for a predetermined semiconductor manufacturing process in a case where the coefficient is less than the predetermined value in the comparing the at least one coefficient of the coefficient of the exponential function and the exponent of the power function, and the predetermined value.

According to an aspect of the present invention, there is provided a method for manufacturing a semiconductor device comprising: forming a resist film by applying a resist solution on a substrate to be processed, the resist solution being qualified as a chemical solution by a method for qualifying chemical solution according to an aspect of the present invention; exposing a part of the resist film; and forming a resist pattern by developing the resist film.

According to another aspect of the present invention, there is provided a method for manufacturing a semiconductor device comprising: forming a resist pattern including a hole region on a substrate to be processed; and shrinking the hole region of the resist pattern by applying a solution including hole region shrinking material on the resist pattern and reacting the solution with the resist pattern, the solution being qualified as a chemical solution by a method for qualifying chemical solution according to an aspect of the present invention.

According to another aspect of the present invention, there is provided a method for manufacturing a semiconductor device comprising: forming a low dielectric constant coating film by applying a solution including low dielectric constant material on a substrate to be processed, the solution being qualified as a chemical solution by a method for qualifying chemical solution according to an aspect of the present invention; forming a mask pattern on the low dielectric constant coating film by lithography process; and forming a low dielectric constant pattern by selectively etching the low dielectric constant coating film using the mask pattern as a mask.

According to another aspect of the present invention, there is provided a method for manufacturing a semiconductor device comprising: forming a ferroelectric coating film by applying a solution including ferroelectric material on a substrate to be processed, the solution being qualified as a chemical solution by a method for qualifying chemical solution according to an aspect of the present invention; forming a mask pattern on the ferroelectric coating film by lithography process; and forming a ferroelectric pattern by selectively etching the ferroelectric coating film using the mask pattern as a mask.

BRIEF DESCRIPTION OF THE SEVERAL VIEWS OF THE DRAWING

FIG. 1 is a graph showing measured result and estimated result of the size and number of particles in a resist solution;

FIG. 2 is a graph showing a relationship between the number of defects on a wafer and the exponent of exponential functions;

FIG. 3 is a graph showing a relationship between the number of defects on a wafer and the exponent of power functions;

FIGS. 4A to 4D are sectional views showing a method for manufacturing a semiconductor device of the first embodiment;

DETAILED DESCRIPTION OF THE INVENTION

Figure 5A:
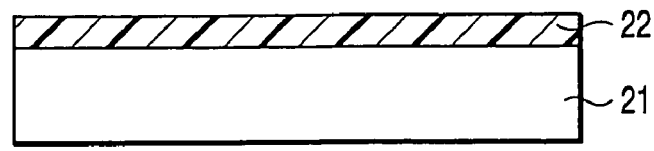
FIGS. 5A to 5C are sectional views showing a method for manufacturing a semiconductor device of the second embodiment.

Hereinafter, embodiments of the present invention will be described with reference to the drawings.

First Embodiment

The inventors prepared resist patterns by using the resist solutions which are the same as lot numbers 1 to 3 shown in Table 1. The resist patterns are formed as follows.

A coating film is formed by applying a resist solution on a wafer, next, exposure process is carried out with respect to the coating film, and thereafter, the resist pattern is formed by carrying out development process with respect to the coating film on which the exposure process had been carried out.

The number of defects per 1 $cm^2$ (defect density) on each resist is measured, and a permitted defect density is determined. The result is shown in Table 2. Note that the measurement of the defect density is carried out by a well-known measuring method using light.

TABLE 2

| Permissible defect density | Measured defect density (Number/$cm^2$) | | |
| --- | --- | --- | --- |
| (Number/$cm^2$) | Lot number 1 | Lot number 2 | Lot number 3 |
| 0.2 Wafer acceptance/ rejection determination | 0.05 Acceptable | 4.08 Rejectable | 0.18 Acceptable |

In Table 2, the defect densities of lot number 1 and lot number 3 which are measured (measured defect densities) are less than the permissible defect density. However, the measured defect density of lot number 2 is over the permissible defect density. Accordingly, wafer acceptance/rejection determinations result in acceptance on lot number 1 and lot number 3, and in rejection with respect to lot number 2. On the other hand, in Table 1, as described above, lot number 1 and lot number 2 are acceptable, and lot number 3 is rejectable (unacceptable). Namely, lot number 2 determined to be acceptable at the resist maker side is determined to be rejectable at the user side, and it is clear that the determined result of the both do not agree with one another.

As this example, when the lot numbers determined to be acceptable by the solution acceptance/rejection determinations at the resist maker side and the lot numbers determined to be acceptable by the wafer acceptance/rejection determinations at the user side do not agree with one another, then, a great compensation is brought about at the resist maker side, and on the other hand, a great loss is brought about at the user side.

The inventors thought that the cause for that the defects on the resist pattern are not necessarily reduced to a large extent even by using a resist solution determined to be acceptable at the resist maker side is particles less than 0.2 µm, i.e., fine particles beyond a measurement limit (measurable minimum fine particle diameter) by a measuring instrument such as a particle counter for counting particles in liquid (particle-in-liquid counter) or the like. Hereinafter, an embodiment which has been achieved in consideration of such a background will be described.

A method for evaluating chemical solution of the present embodiment includes a step for determining the number of particles in liquid for each size of the particles by measurement; a step for expressing a relationship between the size of the particles and the number of particles corresponding to the size by a function based on the number of particles for each size of the particles determined by the measurement; and a step for evaluating influence of particles having the size less than or equal to a measurement limit in the liquid based on the function. The method may further includes a step for determining whether the liquid is acceptable or rejectable in accordance with a magnitude of α (α is described later).

A qualification method for chemical solution of the present embodiment includes a step for determining the number of particles in liquid for each size of the particles by a particle-in-liquid counter; a step for expressing a relationship between the size of the particles and the number of the particles corresponding to the size as an exponential function or a power function; a step for comparing at least one coefficient of a coefficient of the exponential function and an exponent of the power function, and a predetermined value; and a step for qualifying the liquid as a chemical solution used for a predetermined semiconductor manufacturing process in a case where the coefficient is less than the predetermined value in the comparing the at least one coefficient of the coefficient of the exponential function and the exponent of the power function, and the predetermined value.

The exponential function used here is expressed as $$P = P_0 + Ae^{-Z\alpha} \qquad (1)$$

Further, the power function is expressed as $$P = P_0' + A'Z^{-\alpha'} \qquad (2)$$

Here, Z is the size of particles (particle size), and P is the number of particles (particle number). A and A' are coefficients, $\alpha$ (which is called an exponent of the exponential function in the embodiments) and $\alpha'$ are exponents.

In the above-described qualification method for chemical solution, it is not determined whether the chemical solution are acceptable or rejectable on the basis of the number of particles having a specific size, but in the qualification method, the number of particles having the size from fine size to large size are estimated in advance by expressing the number of fine particles by an exponential function or a power function of the size of fine particles as equation (1) and equation (2), next, it is determined whether the chemical solution are acceptable or rejectable on the basis of a coefficient $\alpha$ of an exponential function or a coefficient $\alpha'$ of a power function which shows a rate of change of the particle number with respect to the particle size.

Namely, an accuracy of acceptance/rejection determinations for chemical solution is improved due to the estimation of the number of fine particles lying in a immeasurable range (a range which can not be measured by a measuring instrument) which is obtained by the rate of change of the particle number with respect to the particle size based on the size of fine particles lying in a measurable range (a range which can be measured by a measuring instrument) and the number of fine particles corresponding thereto.

When $\alpha$ (or $\alpha'$) is large, a rate of increase of particles is high, then, the number of particles increases as the size of particles decreases, and many defects occur on a wafer.

On the other hand, When $\alpha$ (or $\alpha'$) is small, the rate of increase of particles is low, then, the number of particles does not increase much as the size of particles decrease, and defects hardly occur on the wafer.

Hereinafter, the present embodiment will be further described.

Here, a qualification method for an ArF resist solution used for an ArF resist process will be described concretely.

First, with respect to various resist solutions used for a 90 nm L/S pattern, a 110 nm hole pattern, and a 90 nm isolated pattern, the relationships between the size of fine particles and the number of fine particles in liquid are acquired by a particle-in-liquid counter (measurable minimum fine particle diameter=0.15 μm).

The size of fine particles are made into 0.02 μm units such as 0.15 to 0.17 μm, 0.17 to 0.19 μm, ..., and the number of fine particles within the respective ranges are measured.

FIG. 1 shows measured result of the number of particles with respect to the size of particles in the resist solution measured by the particle-in-liquid counter, and estimated result of the number of particles less than the measurable minimum fine particle diameter obtained by fitting the measured result with equation (1). In FIG. 1, the outlined circles ○ show the above-described measured result (actually measured values). Further, the full line shows a function expressing the relationship between the size of particles and the number of particles which include the above-described estimated result. The function is y=0.2+87.272e−19.246x (y is the number of particles, and x is the size of particles).

The exponent of the above-described resist solution is $\alpha$=19.245, and has an extremely high accuracy in the fitting with the correlation function $R^2$=0.9979 at that time.

The calculations of exponent $\alpha$ are successively carried out with respect to the respective resist solutions in this way. Note that, at the time of the fitting, A in (equation 1) is appropriately varied such that $R^2$ is made to be 0.99 (which corresponds to an operation of carrying out a base-line correction for particles in liquid).

Next, a resist pattern is formed on a wafer (substrate to be processed) by using these resist solutions. The resist pattern is formed as follows. First, an antireflection coating for preventing reflection at the time of exposure is formed on a Si substrate. Next, a resist film is formed on the antireflection coating. Thereafter, a resist pattern can be obtained by carrying out pattern transfer suitable for the purpose of each resist, and by developing it. Rinsing processing after developing is sufficiently carried out so as not to bring about defects due to the process.

Next, a defect inspection is respectively carried out with respect to each wafer on which the resist pattern is formed. Further, the detected defects is classified, and the defects caused by the resist material are specified, and the number of defects n per 1 $cm^2$ is determined on the basis of a patterning area.

The relationship between the number of defects n determined in this way and the exponent $\alpha$ calculated on the basis of the measured values of the particles in the resist solution is shown in FIG. 2. A good relationship (quadratic equation) between the exponent $\alpha$ expressing the number of particles in the resist solution (x axis) and the number of defects per unit area (y axis) could be found from FIG. 2.

Note that the plotting here has been described without distinction of the purposes of the resists, and further, all the resists in which filtering for a solution (a filter used for refining a solution and a method for refining a solution) is different from each other have been described. Namely it is shown from FIG. 2 that, provided that the resin systems are a same type, those can be expressed by one relationship hardly in dependence on type of photosensitive emulsion, and type or ratio of dissolution suppression base.

With respect to the number of resist defects per unit area which can be permitted for the device, a value of the exponent $\alpha$ necessary to the resist solution could be specified by using the relationship of FIG. 2, and in accordance therewith, it could be easily determined whether or not a resist solution is suitable for preparing a device in the stage of the resist solution.

An example applied to a device of the number of resist defects per unit area which can be permitted <0.5 defects/$cm^2$ will be described hereinafter.

In accordance with FIG. 2, the exponent $\alpha$ of the resist solution which can be applied to the device is $\alpha \leq 24$. On the other hand, the inspection standards in the case of not controlling by this technique are that the number of fine particles of 0.15 μm to 0.18 μm and 0.18 μm to 0.20 μm are respectively less than or equal to 40 particles/ml and 20 particles/ml.

The number of defects on the wafers and the acceptance/rejection table when patternings are executed by using resist solutions which are on/off-specification in a conventional art and resist solutions which are on/off-specification in the present embodiment are arranged in Table 3.

TABLE 3

| | Resist | | | | | |
|---|---|---|---|---|---|---|
| | A | B | C | D | E | F |
| Purpose | Hole | Hole | L/S, L | L/S, L | L/S, L | L/S, L |
| 0.15-0.18 | 39 | 11 | 3.2 | 0.8 | 90 | 7.7 |
| 0.18-0.20 | 15 | 6 | 1.7 | 0.5 | 60 | 5.4 |
| Conventional acceptance/rejection | Acceptance (X) | Acceptance (○) | Acceptance (X) | Acceptance (○) | Rejection (X) | Acceptance (○) |
| $\alpha$ | 27.1 | 20.3 | 26.6 | 18.7 | 21.6 | 16.6 |
| Acceptance/rejection on $\alpha$ | Rejection (○) | Acceptance (○) | Rejection (○) | Acceptance (○) | Acceptance (○) | Acceptance (○) |
| Defect density | 0.70 | 0.12 | 0.61 | 0.36 | 0.45 | 0.33 |
| Acceptance/rejection on wafer | Rejection | Acceptance | Rejection | Acceptance | Acceptance | Acceptance |

The following things can be understood from Table 3. First, the resists A and C result in rejections in the wafer inspections, and on the other hand, the resists A and C result in acceptances in the chemical solution inspections in the conventional method, and it can be understood that the estimate for wafer defects is insufficient. In contrast thereto, according to the present embodiment, the acceptance/rejection determinations result in rejection, which agree with the results of the wafer inspections.

On the other hand, the resist E results in acceptance in the wafer inspection, and in rejection in the chemical solution inspection in the conventional method, and it can be understood that the estimate for the wafer defects is insufficient. In contrast thereto, according to the present embodiment, the acceptance/rejection determinations result in acceptance, which agree with the result of the wafer inspection.

In this way, it is understood that there is the problem in the conventional method that the yield is degraded by using a resist chemical solution which results in rejection in the wafer inspection, or a waste which is such that a resist chemical solution which results in acceptance in the wafer inspection is not used, or the like is brought about.

In contrast thereto, in the present embodiment, the chemical solution inspection had extremely good coincidence with the wafer inspection, and it could be understood that the inspection method is an inspection method having an excellent criterion without degrading the yield by previously detecting defective chemical solution, and without missing non-defective units.

By using the chemical solution determined in this way, the resist pattern could be obtained without degrading the yield by making mistakes in determination for chemical solution, and with a high yield without missing, and the semiconductor element device with high reliability could be obtained.

There is a method as follows as a method for manufacturing a semiconductor device including a step for shrinking a hole region of the resist pattern formed by the method of the present embodiment.

First, as shown in FIG. 4A, a resist pattern 12 including a hole region 13 is formed on a wafer 11.

Next, as shown in FIG. 4B, a chemical solution 14 including a hole region shrinking material is applied on the wafer 11 and the resist pattern 12, and as shown in FIG. 4C, due to the chemical solution 14 including the hole region shrinking material and the resist pattern 12 reacting with each other, the hole region 13 is shrunk, and a hole region 13' is formed.

Thereafter, as shown in FIG. 4D, the hole region shrinking material which has not contributed to the reaction with the resist pattern 12 is removed.

In such a method for shrinking the hole region, by applying the qualification method of the present embodiment to the chemical solution 14 including the hole region shrinking material, the hole region of the resist pattern 12 can be shrunk as desired. In accordance therewith, a finer pattern can be formed with high reliability. To describe concretely, a fine hole pattern and a fine space pattern can be formed, and the open failure in the steps of forming a contact via hole and the process of burying wiring in the space pattern can be greatly improved.

As the chemical solution including the hole region shrinking material, there can be sampled, for example, coating formation material for miniaturizing pattern described in U.S. Pat. Nos. 3,485,183, 3,485,182, 3,476,082, 3,476,081, 3,476, 080, and the like of Tokyo Ohka Kogyo Co., Ltd, coating formation material for miniaturizing pattern process, or Resolution Enhancement Lithography Assisted by Chemical Shrink material (referred to as: RELACS material) which is disclosed by Clariant International AG, and the like.

The concrete example of FIG. 1 uses the exponential function as shown in equation (1) as the fitting equation. However, a power function as shown in equation (2) may be used. In this case, a drawing corresponding to FIG. 2 becomes, for example, as FIG. 3.

Even in a case of using a power function, the high yield can be maintained by determining an upper limit of the exponent $\alpha'$ ($\alpha'$ ulimit) based on the resist defect density permitted in the device, measuring the chemical solution used in the process by the particle-in-liquid counter in advance, selecting the chemical solution having the exponent determined on the basis of the measured values which is less than the $\alpha'$ ulimit and using the chemical solution for the process. Further, functions other than the exponential function and power function may be used.

As the particle-in-liquid counter used for the present embodiment is not particularly limited as far as fine particles in liquid can be measured. For example, the particle-in-liquid counter employing a calculating mechanism for measuring fine particles by analysis technique upon the detection of Mie scattering or a calculating mechanism for measuring fine particles by analysis technique using Doppler effect, and any other mechanisms.

Second Embodiment

Figure 5B:
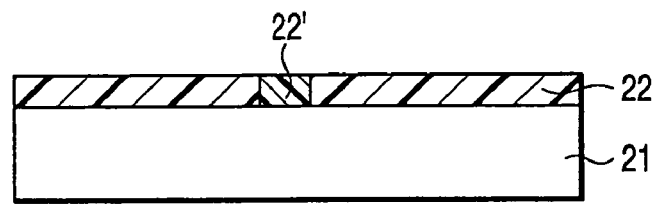
Figure 5C:
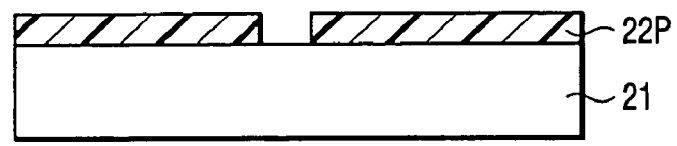

FIGS. 5A to 5C are sectional views showing a method for manufacturing a semiconductor device of the second embodiment.

The method for manufacturing a semiconductor device of the present embodiment includes a step for forming a resist film (first coating film) 22 by applying a resist solution which is qualified as the chemical solution by the first embodiment on a wafer 21 (FIG. 5A), a step for exposing a part 22' of the resist film 22 (FIG. 5B) and a step for forming a resist pattern 22p by developing the resist film 22 (FIG. 5C). The wafer 21 includes, for example, an insulating film and a conductive film which are the objects to be processed.

In the step for forming the resist pattern 22p by developing the resist film 22 which includes the selectively exposed portion, the selectively exposed portion or the portion which is not selectively exposed is removed, and the resist pattern 22p is formed. FIG. 5C shows the former example.

Accordance to the present embodiment, a resist pattern can be formed in a state that a short (connecting of resist patterns) and a defect of a hole are hardly brought about, and moreover, the reliability on an insulating film and wiring which are processed by using the resist pattern as a mask can be greatly improved.

Here, as the light used for exposing the resist film 22 (exposure light), various lights such as an ultraviolet (UV) radiation, a deep-ultraviolet (DUV) radiation, a vacuum ultraviolet (VUV) radiation, X-rays of EUV and the like, a charged particle beam such as an electron beam, an ion beam, and the like can be used. Any material having photosensitivity to the above-described exposure light may be used as the material of the resist film 22.

Further, removement of the resist film 22 can be carried out by wet developing by using an alkaline developing agent or an organic developing agent, and by etching by using reactive ions, and the like.

Further, in a case where the antireflection coating or a conductive film is provided between the resist film 22 and the wafer 21, it is preferable that the chemical solution specified by the first embodiment is used as the solution including antireflective material and the solution including conductive material as well. In the same way, in a case where the antireflection coating or the conductive film is provided upon the resist film 22, it is preferable that the chemical solution specified by the first embodiment is used as the solution including antireflective material and the solution including conductive material as well.

Figure 6:
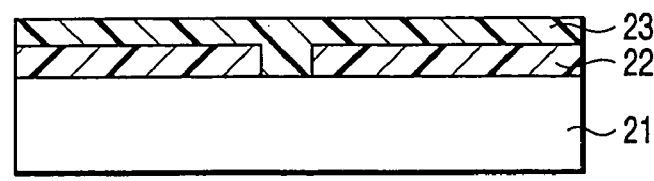
FIG. 6 is a sectional view showing a modified example of the method for manufacturing the semiconductor device of the second embodiment.

Further, as shown in FIG. 6, in a case where the second coating film 23 is formed on the resist pattern 22p after forming the resist pattern 22p, it is preferable that the chemical solution specified by the first embodiment is used as the solution including the second coating film material as well.

Third Embodiment

Figure 7A:
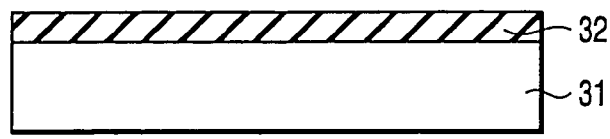
FIGS. 7A to 7C are sectional views showing a method for manufacturing a semiconductor device of the third embodiment.
Figure 7B:
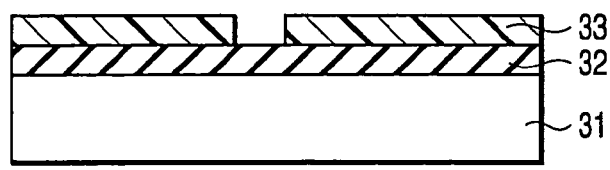
Figure 7C:
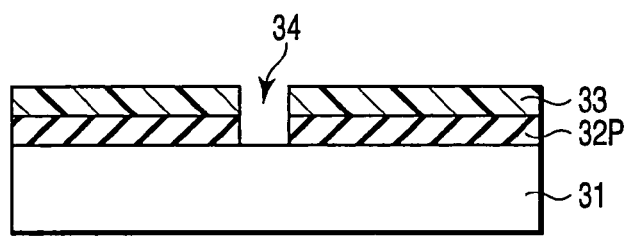

FIGS. 7A to 7C are sectional views showing a method for manufacturing a semiconductor device of the third embodiment.

The method for manufacturing the semiconductor device of the third embodiment includes a step for forming a low dielectric constant coating film 32 by applying a solution including low dielectric constant material which is qualified as the chemical solution by the first embodiment on a wafer (substrate to be processed) 31 (FIG. 7A); a step for forming a mask pattern 33 on the low dielectric constant coating film 32 by lithography process (FIG. 7B); and a step for forming a low dielectric constant pattern 32p by selectively etching the low dielectric constant coating film 32 by using the mask pattern 33 as a mask (FIG. 7C).

According to the present embodiment, the low dielectric constant pattern 32p (insulating film pattern) can be formed in a state that an opening (connecting of insulating film), a defect of opening failure and a lowering of insulation are hardly brought about, therefore, a semiconductor device with high reliability can be manufactured.

Fourth Embodiment

Figure 8A:
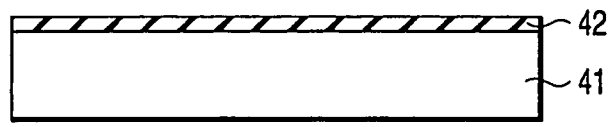
FIGS. 8A to 8C are sectional views showing a method for manufacturing a semiconductor device of the fourth embodiment.
Figure 8B:
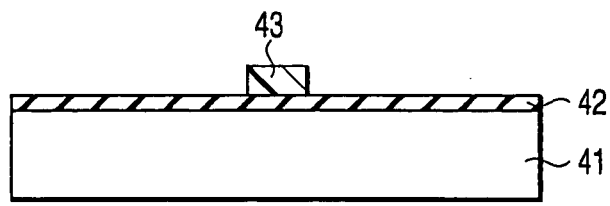
Figure 8C:
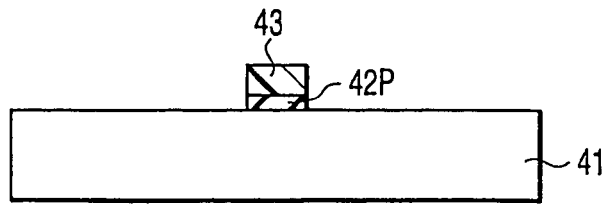

FIGS. 8A to 8C are sectional views showing a method for manufacturing a semiconductor device of the fourth embodiment.

The method for manufacturing a semiconductor device of fourth embodiment includes a step for forming a ferroelectric coating film 42 by applying a solution including ferroelectric material which is qualified as the chemical solution by the first embodiment on a wafer (substrate to be processed) 41 (FIG. 8A); a step for forming a mask pattern 43 on the ferroelectric coating film 42 by lithography process; and a step for forming a ferroelectric pattern 42p by selectively etching the ferroelectric coating film 42 by using the mask pattern 43 as a mask.

According to the present embodiment, the ferroelectric pattern 42p (insulating film pattern) can be formed in a state that a short (connecting of the resist pattern), a defect of opening failure and a increasing of resistance are hardly brought about, therefore, a semiconductor device with high reliability can be manufactured.

The ferroelectric pattern 42p is used for, for example, a ferroelectric capacitor and a capacitor in a ferroelectric memory. The material of the ferroelectric pattern 42p is, for example, PZT (Pb ($Zr_x$, $Ti_{1-x}$O3).

The lithography processes used in the third and fourth embodiments may be any types of lithography processes. It goes without saying that a lithography process as in the second embodiment can be used, and an imprint lithography process technology in which a pattern is formed by stamp may be used.

Note that the present invention is not limited to the embodiments mentioned above.

For example, in the embodiments, the wafer is used as the substrate to be processed, however, it may be another substrate such as a glass substrate and the like. In a case where the glass substrate is used as the substrate to be processed, the method for manufacturing a semiconductor device is made to be, for example, a method for manufacturing a liquid crystal display device (LCD).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for evaluating chemical solution, comprising:
determining number of particles in liquid for each size of the particles by measurement;
expressing a relationship between size of the particles and number of particles corresponding to the size by a function based on the number of particles for each size of the particles determined by the measurement; and
evaluating influence of particles having size less than or equal to a measurement limit in the liquid based on the function,
wherein the function is $P=P_0+Ae^{-Z\alpha}$, where Z is size of particles, P is number of particles, $P_0$ and A are coefficients, and $\alpha$ is an exponent of an exponential function, and
wherein the chemical solution is a resist solution, a solution including low dielectric constant material, or a solution including ferroelectric material.

2. The method for evaluating chemical solution according to claim 1, further comprising:
determining whether the liquid is acceptable or rejectable in accordance with a magnitude of $\alpha$.

3. A method for qualifying chemical solution, comprising:
determining number of particles in liquid for each size of the particles by measurement;
expressing a relationship between size of the particles and number of particles corresponding to the size by a function based on the number of particles for each size of the particles determined by the measurement;

evaluating influence of particles having size less than or equal to a measurement limit in the liquid based on the function, and determining whether the liquid is acceptable or rejectable; and qualifying the liquid as a chemical solution in a case where the liquid is determined acceptable in the determining whether the liquid is acceptable or rejectable, wherein the function is $P=P_0+Ae^{-Z\alpha}$, where Z is the size of particles, P is the number of particles, $P_0$ and A are coefficients, and $\alpha$ is an exponent of an exponential function, and wherein the chemical solution is a resist solution, a solution including low dielectric constant material, or a solution including ferroelectric material.

4. The method for qualifying chemical solution according to claim 3, wherein the determining whether the liquid is acceptable or rejectable is determined in accordance with a magnitude of $\alpha$.

* * * * *